United States Patent
Mahesh et al.

(10) Patent No.: US 8,099,296 B2
(45) Date of Patent: Jan. 17, 2012

(54) SYSTEM AND METHOD FOR RULES-BASED CONTEXT MANAGEMENT IN A MEDICAL ENVIRONMENT

(75) Inventors: Prakash Mahesh, Schaumburg, IL (US); Mark M. Morita, Arlington Heights, IL (US); Thomas A. Gentles, Algonquin, IL (US)

(73) Assignee: General Electric Company, Schenectady, NY (US)

( * ) Notice: Subject to any disclaimer, the term of this patent is extended or adjusted under 35 U.S.C. 154(b) by 1901 days.

(21) Appl. No.: 10/956,171

(22) Filed: Oct. 1, 2004

(65) Prior Publication Data

US 2006/0074633 A1   Apr. 6, 2006

(51) Int. Cl.
*G06Q 50/00* (2006.01)

(52) U.S. Cl. .......................................................... 705/2

(58) Field of Classification Search .................. 705/2, 4; 345/744

See application file for complete search history.

(56) References Cited

U.S. PATENT DOCUMENTS

| | | | |
|---|---|---|---|
| 6,889,363 B2 | 5/2005 | Maloney | |
| 2002/0122057 A1* | 9/2002 | Maloney | 345/744 |

FOREIGN PATENT DOCUMENTS

| | | |
|---|---|---|
| JP | 2002358361 | 12/2002 |
| JP | 2005209186 | 8/2005 |
| WO | 0248865 A2 | 6/2002 |
| WO | 02075512 | 9/2002 |

OTHER PUBLICATIONS

European Patent Office, "Communication pursuant to Article 94(3) EPC," issued in connection with European Patent Application No. 05 803 112.1, dated Jan. 19, 2010 (4 pages).

English translation of Japanese Preliminary Rejection, issued in connection with Japanese Application No. 2008-534507, mailed on Mar. 22, 2011. (1 page).

* cited by examiner

*Primary Examiner* — Gerald J. O'Connor
*Assistant Examiner* — John Pauls
(74) *Attorney, Agent, or Firm* — Hanley, Flight & Zimmerman, LLC

(57) ABSTRACT

Certain embodiments of the present invention provide a method and system for improved diagnostic reading and workflow in a healthcare environment using rules-based context management. In an embodiment, the system includes a plurality of information sources, wherein each of the plurality of information sources includes information. The system also includes a rules engine including at least one rule governing at least one of availability and presentation of information. In addition, the system includes a context manager for obtaining information from the plurality of information sources based on a query and filtering the information based on the at least one rule. In an embodiment, the information sources include an information system and/or an imaging system, for example.

16 Claims, 2 Drawing Sheets

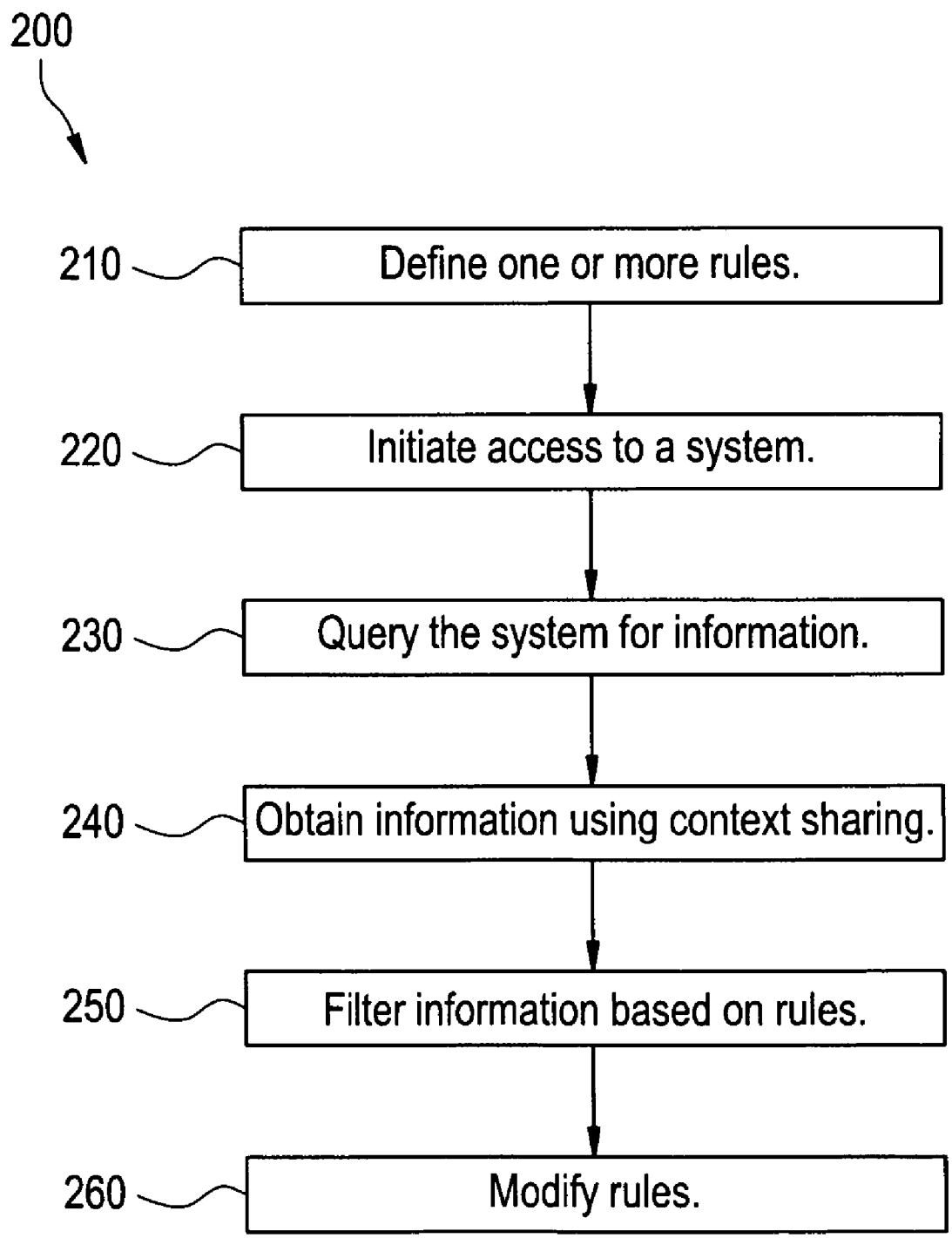

SYSTEM AND METHOD FOR RULES-BASED CONTEXT MANAGEMENT IN A MEDICAL ENVIRONMENT

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to context management in a healthcare environment. In particular, the present invention relates to use of rules-based context management to improve diagnostic reading and workflow in a healthcare environment.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitate operation of an imaging system and related services by an individual operator would be highly desirable.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Currently, a practitioner must log on to different systems and search for a patient to retrieve information from the system on that patient. For example, if a patient complains of chest pain, a chest x-ray is taken. Then the radiologist logs on to other systems to search for the patient and look for specific conditions and symptoms for the patient. Thus, the radiologist may be presented with a large amount of information to review.

Depending upon vendors and systems used by a practitioner, practitioners, such as radiologists or cardiologists, have only a few options to reference the tools available. First, a request for information from the available tools may be made in paper form. Second, a practitioner may use different applications, such as a radiologist information system (RIS), picture archiving and communication system (PACS), electronic medical record (EMR), healthcare information system (HIS), and laboratory information system (LIS), to search for patients and examine the information electronically.

In the first case, the practitioner shifts his or her focus away from a reading workstation to search and browse through the paper, which in most cases includes many pieces of paper per patient. This slows down the practitioner and introduces a potential for errors due to the sheer volume of paper. Thus, a system and method that reduce the amount of paper being viewed and arranged by a practitioner would be highly desirable.

In the second case, electronic information systems often do not communicate well across different systems. Therefore, the practitioner must log on to each system separately and search for the patients and exams on each system. Such a tedious task results in significant delays and potential errors. Thus, a system and method that improve communication and interaction between multiple electronic information systems would be highly desirable.

Additionally, even if systems are integrated using mechanisms such as Clinical Context Object Workgroup (CCOW) to provide a practitioner with a uniform patient context in several systems, the practitioner is still provided with too much information to browse through. Too much information from different applications is provided at the same time and slows down the reading and analysis process. There is a need to filter out application components that a user will not need in a routine workflow. Thus, a system and method which manage information provided by multiple systems would be highly desirable.

Furthermore, if a technologist is performing a radiology or cardiology procedure, for example, the technologist typically accesses multiple applications to obtain information prior to the procedure. In a digital environment, information resides in a plurality of disparate systems, such as a RIS and a PACS. Currently, the technologist must access each system and search for the information by clicking many tabs and buttons before having access to all of the information needed to start the procedure. Often, such an effort by a technologist to obtain information for a procedure results in a decrease in productivity due to the time involve and/or a decrease in information quality due to the time involved to do a thorough search. Thus, a system and method which improve searchability and access to data would be highly desirable.

Additionally, referring physicians use many computerized applications for patient care. In radiology, a physician may look at information from RIS, PACS, EMR, and Computer Physician Order Entry (CPOE), for example. The referring physician typically accesses multiple applications to get all of the information needed before, during and/or after the patient consult and follow-up. For example, in a digital environment, the referring doctor refers to a RIS for results from a current procedure, prior procedures, and/or a web-based image viewer, such as a PACS, for viewing any current and prior images. The doctor may access a CPOE to order any follow-up exams. The referring physician opens the RIS, PACS, and CPOE to search for the information by clicking many tabs and buttons before having access to the information. Thus, there is a need for a system and method which improve searchability and access to data.

Thus, there is a need for a system and method to improve diagnostic reading and workflow in a healthcare environment

BRIEF SUMMARY OF THE INVENTION

Certain embodiments of the present invention provide a method and system for improved diagnostic reading and workflow in a healthcare environment using rules-based context management. In an embodiment, the system includes a plurality of information sources, wherein each of the plurality of information sources includes information. The system also includes a rules engine including at least one rule governing at least one of availability and presentation of information. In addition, the system includes a context manager for obtaining information from the plurality of information sources based on a query and filtering the information based on the at least one rule. In an embodiment, the information sources include an information system and/or an imaging system, for example.

The system may also include an authentication module for authenticating access to at least one of the context manager and at least one of the plurality of information sources. In an embodiment, the system also includes a plurality of perspectives, where each perspective saves a relation with at least one of the plurality of information sources. A medical perspectives manager associates at least one information source with a perspective and allows a user to access the at least one associated information source using the perspective.

In an embodiment, the rules engine includes a plurality of sets of rules for a plurality of groups. The rules engine may adapt the rule(s) based on a prior observation and/or user input, for example. In an embodiment, the context manager includes a plurality of rules-based contexts for a plurality of groups.

Certain embodiments of a method for rules-based context management in a healthcare environment include sharing a context between information systems to connect a plurality of disparate information systems, retrieving information from at least one of the information systems based on a request, and filtering the information based on at least one rule. The method may also include defining a set of rules for filtering information from the information systems. Also, the method may include adapting the set of rules based on a prior observation and/or user input, for example. Additionally, the method may include selecting a context for retrieving the information. The method may include selecting a perspective for retrieving the information. In an embodiment, the method includes authenticating access to the information.

Certain embodiments of a method for providing rules-based context management in a healthcare environment include creating at least one context for retrieving information from at least one information source, defining set of at least one rule for processing information, and allowing retrieval of information in the context(s) using the rule(s). The method may further include selecting a context from a plurality of contexts for retrieving information. Also, the method may include selecting a set of rules from a plurality of rules for processing information. The method may include adapting at least one rule based on a prior observation and/or user input, for example. The method may also include selecting a perspective for organizing retrieved information.

In an embodiment, a computer-readable storage medium includes a set of instructions for a computer. The set of instructions includes a context management routine for defining a context coordinating a plurality of information sources, a rules engine routine for defining rules for processing information, and an information retrieval routine for forming an information query in the context and filtering the information based on the rules. The set of instructions may also include a perspectives routine for organizing the information for a user.

BRIEF DESCRIPTION OF SEVERAL VIEWS OF THE DRAWINGS

FIG. 2 illustrates a flow diagram for a method for improved diagnostic reading and workflow using rules-based context management in accordance with an embodiment of the present invention.

Figure 1:
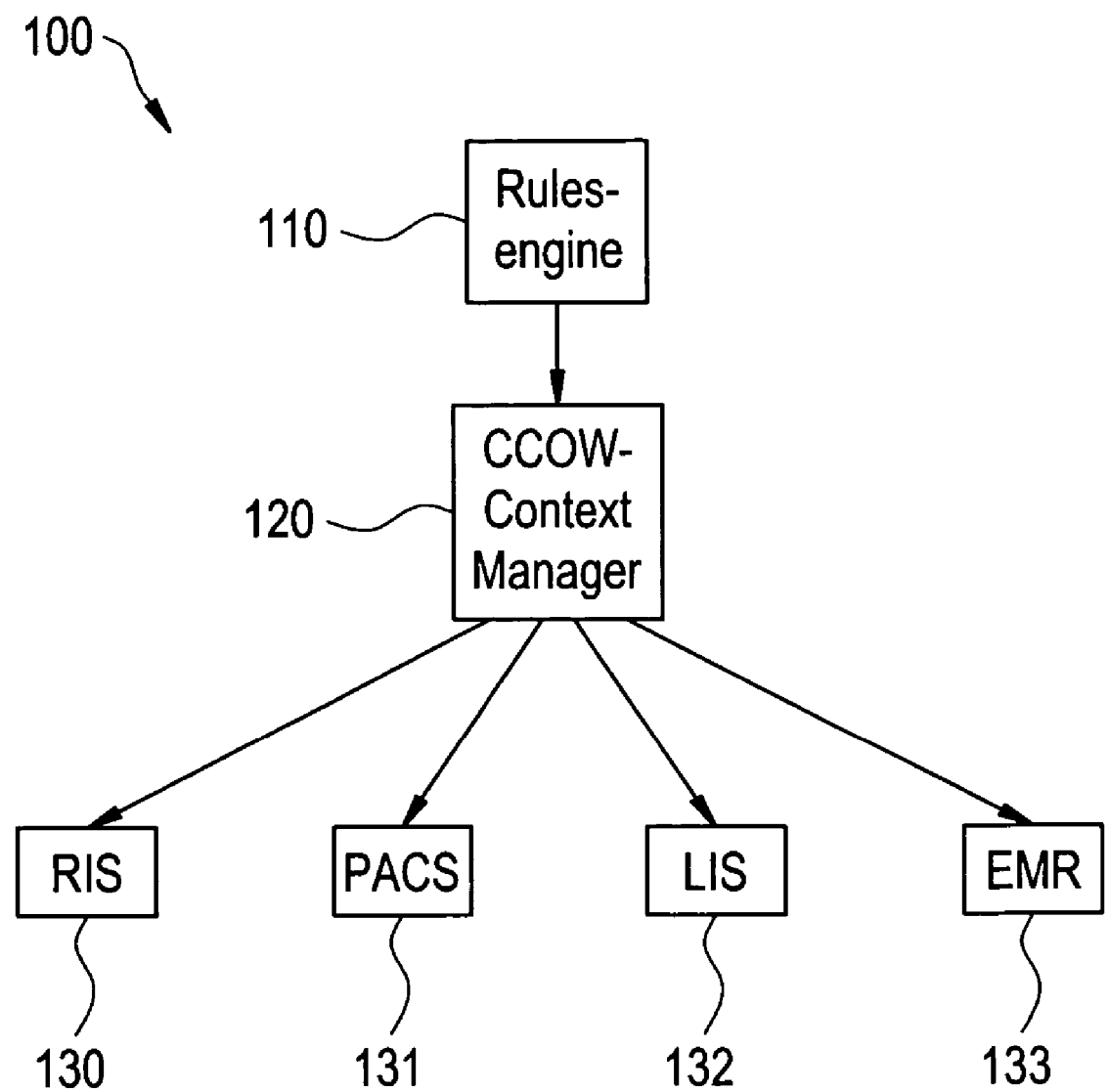
FIG. 1 illustrates a rules-based context management system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a rules-based context management system 100 used in accordance with an embodiment of the present invention. The system 100 includes a rules engine 110, a context manager 120, and a plurality of information systems 130, 131, 132, 133. Information systems 130-133 may include a radiology information system (RIS) 130, a picture archiving and communication system (PACS) 131, a laboratory information system (LIS) 132, and/or an electronic medical record (EMR) 133, for example. The context manager 120 may be a clinical context object workgroup (CCOW) context manager, for example. The components of the system 100 may communicate via wired and/or wireless connections on one or more processing units, such as computers, medical systems, storage devices, custom processors, and/or other processing units. In an embodiment, the components of the system 100 are integrated into a single unit.

The system 100 may be used to provide an integrated solution for application execution and/or information retrieval based on rules and context sharing. For example, context sharing allows information and/or configuration options/settings, for example, to be shared between system environments. Rules, for example, may be defined dynamically and/or loaded from a library to filter and/or process information generated from an information system and/or an application.

The context manager 120 may be used to create patient and/or examination context sharing between information systems 130-133. The context manager 120 may be an integrated or standalone software and/or hardware manager for context sharing between information systems 130-133. The manager 120 may also provide relevant information within a patient and/or examination context based on rules. The context manager 120 may be a context manager such as CCOW, which uses an HL7 standard to support user and patient context sharing, or other context management system. Context sharing allows information from a plurality of systems to be combined in a single context or setting. For example, information on a particular patient may be extracted from a RIS, a PACS, and an EMR. The manager 120 works in conjunction with the rules engine 110 to extract information from systems 130-133 using extensible markup language (XML), simple object access protocol (SOAP), and/or other protocol, for example. The manager 120 and/or rules engine 110 may include a user interface, such as a graphical or voice command user interface, to allow a user to access components and features of the system 100.

In an embodiment, the context manager 120 includes and/or communicates with an authentication unit. The authentication unit may include software and/or hardware to verify a user's right to access one or more of the manager 120, information systems 130-133, and/or rules engine 110. In an embodiment, authentication via the context manager 120 allows access to relevant information systems 130-133 and other applications for a user. If a user logs on to a system running the context manager 120, a rule may be created and saved to log onto certain information systems 130-133 to access the user's preferred information.

For example, a physician may prefer to look at labs, allergies and medication. Thus, a rule is created to log on to an LIS and HIS for labs, allergies and medication when the physician logs onto the system 100. Applications, such as LIS and HIS, are moved to a correct patient context. Along with the context and based on rules, the LIS and HIS display pertinent information for a patient. For example, the applications display all lab results for the patient for a specific date. The applications also display all complete blood count (CBC) data for the patient for the date. As another example, rules may filter patient alert data for a specific date range and/or specific disease type. Thus, from the same workstation using the system 100, a user may look at a RIS for relevant prior reports, search a PACS for relevant prior images, and/or examine a LIS and/or HIS for specific information, all based on context sharing and rules. As a result, diagnosis and diagnostic reports may be reached more quickly and more accurately.

Rules for the context manager 120 may be created in a variety of ways. Rules may be generated automatically by the rules engine 110 based on preset parameters and/or observed data, for example. Rules may also be created by a system administrator or other user. Rules may be changed to provide different information for diagnosis. Rules also may be manually and/or automatically adapted based on experiences. Applicable rules from the rules engine 110 are transmitted to the context manager 120.

A user may log on any one of the connected systems and access information found on all of the connected systems through context sharing. The information may be filtered for easier, more effective viewing. Thus, a user may access desired information from a plurality of systems with unwanted information removed.

In operation, a user, such as a radiologist or cardiologist, accesses the context manager 120 via a RIS/PACS system, for example. RIS and PACS systems may be integrated into a single system, for example, with shared patient and exam contexts. Thus, the user access relevant prior history for a patient (e.g., images and reports). For example, the radiologist may log on to the RIS/PACS system which retrieves and integrates information from different systems based on an EMR number. Automatic login to one or more systems/applications may be accomplished via context management.

However, a large quantity of information may result from such context sharing. All of the information may be linked at the patient level, for example. The context manager 120 provides relevant prior history and other information, for example, based on rules from the rules engine 110. Rules may be applied to images, reports, and other data.

Rules-based context management allows information to be provided to a practitioner for a patient based on certain rules. Rules may be used by a practitioner and/or system to define a context for information. For example, if a radiologist only wishes to see lab results for two months, a rule may be created in the rules engine 110 to only provide the previous two months of lab results to the radiologist. Rules may be created based on time period, examination type, disease type, system type, etc. Rules may be predefined and/or created on the fly by the practitioner. Rules may also be automatically generated and/or modified by the rules engine 110 based on practitioner usage patterns and/or preferences, for example.

For example, a referring physician preparing for a patient looks at a requested procedure, prior clinical conditions of the patient, protocols from a radiologist, and relevant prior images, current reports and current images. The rules engine 110 allows the physician to set up a rule for exams to provide procedure and report information from an RIS, clinical conditions from an EMR, protocols from the RIS, and current images and relevant prior images from a PACS, for example. When the physician meets with the patient, the rules engine 110 may trigger the context manager 120 with information that determines a context. The context is driven by the context manager 120 to connected applications and relayed to the physician's desktop. Thus, by selecting an exam, the referring physician sees a variety of information.

For example, a computed tomography (CT) technologist preparing to scan a patient reviews at a requested procedure, prior clinical conditions of the patient, protocols from a radiologist, and relevant prior images. The technologist may use the rules engine 110 to define a rule for CT exams to provide procedure information from a RIS, clinical conditions from an EMR, protocols from the RIS, and relevant prior images from a PACS. When the technologist selects to begin the procedure, the rules engine 110 triggers the context manager 120 with information deciding the context for the exam. The context is driven by the context manager 120 to connected applications and related to the technologist's desktop to enable the technologist to have access to relevant information by selecting an exam.

In an embodiment, the manager 120 may work together with a perspectives management system for handling multiple applications and workflow. The perspectives management system allows various perspectives to be defined which save workflow steps and other information for a particular user. Perspectives may be used to save visual component positioning information and interactions based on workflow, for example. Perspectives allow relevant information to be presented to a user. One example of a perspectives management system is described in a U.S. patent application filed on Oct. 1, 2004, entitled "System and Method for Handling Multiple Radiology Applications and Workflows", with inventors Prakash Mahesh and Mark Ricard, which is herein incorporated by reference in its entirety.

FIG. 2 illustrates a flow diagram for a method 200 for improved diagnostic reading and workflow using rules-based context management in accordance with an embodiment of the present invention. First, at step 210, one or more rules are defined. Rules may be defined for a particular user or group of users (e.g., surgeons, radiologists, cardiologists, etc.), for a particular use or group of uses (e.g., image-guided surgery, radiology reading, structured reporting, examination, etc.), for a particular modality (e.g., x-ray, ultrasound, magnetic resonance imaging, etc.), and/or for a particular platform (e.g., a PACS, an integrated RIS/PACS, an imaging system, etc.), for example. Rules may be defined by software, by a user, and/or by a system administrator, for example. New rules may be created, and/or existing rules may be modified.

Then, at step 220, a user initiates access to a system, such as an information system or clinical workstation. Access to a system may include authentication at the system and/or authentication at additional connected systems. Authentication may occur manually and/or automatically based on input or stored information.

Next, at step 230, a user queries the system for information. For example, the user queries the system regarding a patient. At step 240, context sharing is used to obtain information regarding the query from a variety of connected systems. For example, context sharing is used to obtain patient information from an EMR, PAC, RIS, HIS, and LIS.

Then, at step 250, the queried information is filtered based on the defined rules applicable to the user. That is, rules defined for the user, group of users, modality, and/or platform, for example, are used to refine and customize the data delivered to the user. The information may be filtered with rules before and/or after the information is obtained from the plurality of information sources. Thus, the user is presented with relevant, requested information. The filtered information may be displayed for the user, stored, and/or routed to another program, for example. In an embodiment, the user may organize the information presented based on perspectives which save visual component positioning and interactions based on workflow, for example.

At step 260, rules may be modified based on commands executed at the system and/or manual modification by the user. For example, rules may automatically be refined by the context manager 120 and rules engine 110 based on observed requests and options selected by the user. Additionally, for example, the user may manually add, delete, and/or modify rules stored in the rules engine 110.

Thus, certain embodiments unify a variety of information systems and other applications. Certain embodiments filter information available to a user based on rules. Certain embodiments provide rules-based context sharing among a plurality of systems including RIS, PACS, CVIS (Cardiovascular Information System), EMR, LIS, HIS, and/or other applications. Certain embodiments facilitate increased productivity of a radiologist, cardiologist, or other user reading exams that use relevant information from other information systems. Increased productivity includes a speed in which a diagnosis may be performed and an accuracy of reports produced based on the diagnosis.

In certain embodiments, rules allow information and workflow to be filtered. A user may store and toggle between contexts and sets of rules. In certain embodiments, a user may toggle between sets of rules without touching a keyboard or mouse using a technique such as voice command and/or gaze tracking. Alternatively, a user may toggle between rules using a single click from a mousing device or a button. Thus, certain embodiments allow a user to view only the information he or she wants in the workflow he or she wants. Certain embodiments allow a user to manage the number of applications being accessed at a given time. Certain embodiments provide a rules and context based integration between information systems and applications.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A rules-based context management system, the system comprising:
   a computer processor; and a memory storing a set of instructions for execution by the processor to provide:
   a plurality of information sources, wherein each of the plurality of information sources includes information;
   a rules engine to include at least one rule governing availability and presentation of information;
   a context manager to obtain information from the plurality of information sources based on a query and to filter the information based on the at least one rule, wherein the context manager and the rules engine are to customize presentation of the information to a user from the plurality of information sources within a single patient context based on the at least one rule from the rules engine;
   a plurality of perspectives, each perspective saving a relation with at least one of the plurality of information sources, each perspective saving workflow steps, component positioning information, and interaction for a user, each perspective saving visual component positioning information and interaction based on the workflow steps; and
   a medical perspectives manager for associating at least one information source with a perspective, wherein the medical perspectives manager allows the user to access the at least one associated information source using the perspective,
   at least one of the plurality of information sources, the rules engine, the context manager, and the medical perspectives manager implemented using the processor and the set of instructions stored on the memory.

2. The system of claim 1, further comprising an authentication module for authenticating access to at least one of the context manager and at least one of the plurality of information sources.

3. The system of claim 1, wherein the plurality of information sources includes at least one of an information system and an imaging system.

4. The system of claim 1, wherein the rules engine includes a plurality of sets of rules for a plurality of groups.

5. The system of claim 1, wherein the rules engine adapts the at least one rule based on at least one of a prior observation and user input.

6. The system of claim 1, wherein the context manager includes a plurality of rules-based contexts for a plurality of groups.

7. A computer-implemented method for rules-based context management in a healthcare environment, the method comprising:
   sharing a context between information systems using a context manager to connect a plurality of disparate information systems;
   retrieving information, using a processor, from at least one of the information systems based on a request;
   selecting a perspective for organizing retrieved information, the perspective saving workflow steps, component positioning information, and interaction for a user, each perspective saving visual component positioning information and interaction based on the workflow steps; and
   filtering the information, using a processor, based on at least one rule provided by a rules engine to customize presentation of the information to the user from the plurality of information systems within a single patient context based on the at least one rule from the rules engine.

8. The method of claim 7, further comprising defining a set of rules for filtering information from the information systems.

9. The method of claim 7, further comprising adapting the set of rules based on at least one of a prior observation and user input.

10. The method of claim 7, further comprising selecting a context for retrieving the information.

11. The method of claim 7, further comprising authenticating access to the information.

12. A computer-implemented method for providing rules-based context management in a healthcare environment, the method comprising:
   creating, using a processor, at least one context for retrieving information from at least one information source;
   defining set of at least one rule for processing information, the set of at least one rule provided by a rules engine to customize presentation of information to a user from the at least one information source within a single patient context based on the at least one rule from the rules engine;
   allowing retrieval of information in the at least one context using a processor and the at least one rule for customized presentation of the information to the user; and
   selecting a perspective for organizing retrieved information, each perspective saving workflow steps, component positioning information, and interaction for a user, each perspective saving visual component positioning information and interaction based on the workflow steps.

13. The method of claim 12, further comprising selecting a context from a plurality of contexts for retrieving information.

14. The method of claim 12, further comprising selecting a set of rules from a plurality of rules for processing information.

15. The method of claim 12, further comprising adapting at least one rule based on at least one of prior observation and user input.

16. A tangible computer-readable storage medium including a set of instructions for a computer, the set of instructions comprising:
   a context management routine for defining a context coordinating a plurality of information sources;
   a rules engine routine for defining rules for processing information, the rules provided by the rules engine routine to customize presentation of information to a user from the at least one information source within a single patient context based on the at least one rule from the rules engine;
   an information retrieval routine for forming an information query in the context and filtering the information based on the rules for customized presentation of the information to the user; and
   a perspectives routine for organizing the information for a user, each perspective saving workflow steps, component positioning information, and interaction for a user, each perspective saving visual component positioning information and interaction based on the workflow steps.

* * * * *